(12) United States Patent
Sherman et al.

(10) Patent No.: US 7,572,405 B2
(45) Date of Patent: Aug. 11, 2009

(54) METHOD FOR MANUFACTURING MICROSTRUCTURES HAVING HOLLOW MICROELEMENTS USING FLUIDIC JETS DURING A MOLDING OPERATION

(75) Inventors: Faiz Feisal Sherman, West Chester, OH (US); Vladimir Gartstein, Cincinnati, OH (US)

(73) Assignee: Corium International Inc., Redwood City, CA (US)

( * ) Notice: Subject to any disclaimer, the term of this patent is extended or adjusted under 35 U.S.C. 154(b) by 560 days.

(21) Appl. No.: 10/853,658

(22) Filed: May 25, 2004

(65) Prior Publication Data

US 2006/0076718 A1    Apr. 13, 2006

Related U.S. Application Data

(60) Provisional application No. 60/475,085, filed on Jun. 2, 2003.

(51) Int. Cl.
*B29C 43/02* (2006.01)
*B29C 1/48* (2006.01)

(52) U.S. Cl. .................... 264/504; 264/154; 264/319

(58) Field of Classification Search .............. None
See application file for complete search history.

(56) References Cited

U.S. PATENT DOCUMENTS

| | | | |
|---|---|---|---|
| 3,873,255 A * | 3/1975 | Kalwaites | .................. 28/104 |
| 4,151,240 A | 4/1979 | Lucas et al. | |
| 4,342,314 A | 8/1982 | Radel et al. | |
| 4,395,215 A | 7/1983 | Bishop | |
| 4,463,045 A | 7/1984 | Ahr et al. | |
| 4,509,908 A | 4/1985 | Mullane, Jr. | |
| 4,609,518 A | 9/1986 | Curro et al. | |
| 5,244,711 A * | 9/1993 | Drelich et al. | .............. 428/113 |
| 5,536,263 A | 7/1996 | Rolf et al. | |
| 5,567,376 A | 10/1996 | Turi et al. | |
| 6,024,553 A | 2/2000 | Shimalla | |
| 6,256,533 B1 | 7/2001 | Yuzhakov et al. | |
| 6,312,612 B1 | 11/2001 | Sherman et al. | |
| 6,379,324 B1 | 4/2002 | Gartstein et al. | |
| 6,451,240 B1 | 9/2002 | Sherman et al. | |
| 6,471,903 B2 | 10/2002 | Sherman et al. | |
| 6,565,532 B1 | 5/2003 | Yuzhakov et al. | |
| 6,591,124 B2 | 7/2003 | Sherman et al. | |
| 6,652,478 B1 | 11/2003 | Gartstein et al. | |
| 6,663,820 B2 | 12/2003 | Arias et al. | |
| 2002/0045859 A1 | 4/2002 | Gartstein et al. | |
| 2002/0045907 A1 | 4/2002 | Sherman et al. | |
| 2002/0133129 A1 * | 9/2002 | Arias et al. | ................. 604/272 |
| 2002/0177858 A1 | 11/2002 | Sherman et al. | |
| 2003/0220656 A1 | 11/2003 | Gartstein et al. | |
| 2004/0087992 A1 | 5/2004 | Gartstein et al. | |

FOREIGN PATENT DOCUMENTS

WO     WO 00/74765 A1     12/2000

* cited by examiner

*Primary Examiner*—Monica A Huson
(74) *Attorney, Agent, or Firm*—Mintz Levin Cohn Ferris Glovsky & Popeo, P.C.

(57) ABSTRACT

A method is provided for constructing microstructures that can penetrate skin layers, in which the microelements are formed during a molding process while fluidic jets produce openings in the microelements. The structures used in the molding process are formed by tooling that creates the shapes of the microelements in a material deposition step, and also creates the sizes and shapes of the openings that will be formed by the fluidic jets.

19 Claims, 4 Drawing Sheets

METHOD FOR MANUFACTURING MICROSTRUCTURES HAVING HOLLOW MICROELEMENTS USING FLUIDIC JETS DURING A MOLDING OPERATION

CROSS REFERENCE TO RELATED APPLICATION

This application claims the benefit of U.S. Provisional Application No. 60/475,085, filed Jun. 2, 2003.

TECHNICAL FIELD

The present invention relates generally to manufacturing microstructures and is particularly directed to microstructures of the type which contain a substrate and an array of microelements with through-holes. The invention is specifically disclosed as a method for constructing microstructures that can penetrate skin layers, in which the microelements are formed during a molding process while fluidic jets produce openings in the microelements. The structures used in the molding process are formed by tooling that creates the shapes of the microelements, and also creates the sizes and shapes of the openings that will be formed by the fluidic jets. In some embodiments, the sizes and shapes of the openings are determined by a mask plate, while in another embodiment, no separate mask plate is used. In some embodiments, the molding structures are formed using a deposition process, while in other embodiments, they are formed by injection molding, embossing, or die casting. In one of the embodiments, the microstructures are formed by depositing a material onto the surface of a tooling of a particular shape, and then after being released from the tooling, placing a second material that acts as the mask over the first tooling-formed material. A moldable material is then placed against the combination of the two materials, and during this procedure a high pressure gas or liquid is directed through the holes (i.e., forming the fluidic jets) in the mask to form through-holes in the moldable material. Once the moldable material is released, the result will be an array of hollow microelements that protrude from a substrate. In one of the alternative embodiments (without the separate mask), the first material has openings that will be of a proper size for use themselves as a "mask" for the directed high pressure gas or liquid.

BACKGROUND OF THE INVENTION

Microstructures containing an array of microelements have been disclosed in various patent publications, many of which include openings that allow a fluid exchange between the top and bottom surfaces of the microelement array. The individual microelements typically are designed to penetrate the stratum corneum of animal skin, or to penetrate some other type of membrane. Once the penetration has been accomplished, a fluid (e.g., liquid drugs) can be dispensed into the body from a reservoir in the microstructure, or in the reverse direction, a body fluid can be sampled into such a reservoir in the microstructure.

The proper size and shape of the microelements depends upon many factors, and for some applications (e.g., drug delivery or body fluid sampling through human skin), several different sizes, and especially shapes, will suffice. Some applications of microstructures do not require openings; however, for those applications that do need openings, it is important to find a way to manufacture such microstructures in an inexpensive (and high-volume) manner, within tolerable accuracy to lower reject rates during the manufacturing of these devices.

Various sizes and shapes of microstructures have been disclosed by the present inventors, in commonly-assigned United States Patent applications, as noted below. The documents listed below are incorporated herein by reference, in their entirety: INTRACUTANEOUS MICRONEEDLE ARRAY APPARATUS, Ser. No. 09/328,947, filed on Jun. 9, 1999; APPARATUS AND METHOD FOR USING AN INTRACUTANEOUS MICRONEEDLE ARRAY, Ser. No. 09/329,025, filed on Jun. 9, 1999, now U.S. Pat. No. 6,256,533 B1, which issued Jul. 3, 2001; APPARATUS AND METHOD FOR MANUFACTURING AN INTRACUTANEOUS MICRONEEDLE ARRAY, Ser. No. 09/328,946, filed on Jun. 9, 1999, now U.S. Pat. No. 6,312,612 B1, which issued Nov. 6, 2001; INTRACUTANEOUS EDGED MICRONEEDLE APPARATUS, Ser. No. 09/580,780, filed on May 26, 2000; INTRACUTANEOUS MICRONEEDLE ARRAY APPARATUS, Ser. No. 09/580,819, filed on May 26, 2000; METHOD OF MANUFACTURING AN INTRACUTANEOUS MICRONEEDLE ARRAY, Ser. No. 09/579,798, filed on May 26, 2000; METHOD OF MANUFACTURING MICRONEEDLE STRUCTURES USING SOFT LITHOGRAPHY AND PHOTOLITHOGRAPHY, Ser. No. 09/808,534, filed on Mar. 14, 2001; MICROSTRUCTURES FOR TREATING AND CONDITIONING SKIN, Ser. No. 09/952,403, filed on Sep. 14, 2001; MICROSTRUCTURES FOR DELIVERING A COMPOSITION CUTANEOUSLY TO SKIN, Ser. No. 09/952,391, filed on Sep. 14, 2001; MICROSTRUCTURES FOR DELIVERING A COMPOSITION CUTANEOUSLY TO SKIN USING ROTATABLE STRUCTURES, Ser. No. 10/216,148, filed on Aug. 9, 2002; and METHOD FOR MANUFACTURING MICROSTRUCTURES HAVING MULTIPLE MICROELEMENTS WITH THROUGH-HOLES, Ser. No. 10/373,251, filed on Feb. 24, 2003.

It would be beneficial to provide an improved and low-cost, high-volume method of manufacturing microstructures with openings that extend through the substrate and through the individual microelements.

SUMMARY OF THE INVENTION

Accordingly, it is an advantage of the present invention to provide a methodology for forming a microstructure having an array of microelements with openings, in which the microstructure is formed by first depositing a material on a tooling (such as a die or mold) of a predetermined shape up to a predetermined thickness, in which the tooling exhibits a plurality of protrusions that cause openings to be created in the first material, then releasing the first material and placing a second material thereupon which acts as a mask over the first material, the mask having openings at predetermined locations, then placing a moldable (third) material against a surface formed by both of the first material and second material (mask) layers, and finally directing a high pressure gas or liquid through the mask openings to form holes in the moldable material, then solidifying and demolding the moldable material, which will exhibit an array of hollow microstructures.

Accordingly, it is another advantage of the present invention to provide a methodology for forming a microstructure having an array of microelements with openings, in which the microstructure is formed by first depositing a material on a tooling (such as a die or mold) of a predetermined shape up to a predetermined thickness, in which the tooling exhibits a plurality of protrusions that cause openings to be created in the first material, then releasing the material and placing a second material thereupon which acts as a mask over the first material, the mask having openings at predetermined locations, in which the mask includes protrusions that are directed toward openings formed in the first material, then placing a moldable (third) material against a surface formed by both of the first material and second material (mask) layers, and finally directing a high pressure gas or liquid through the mask openings to form holes in the moldable material, then solidifying and demolding the moldable material, which will exhibit an array of hollow microstructures that protrude from a substrate, and in which the hollow microelements exhibit an enlarged inner opening (or diameter) near the tips of the individual microelements.

It is yet another advantage of the present invention to provide a methodology for forming a microstructure having an array of microelements with openings, in which the microstructure is formed by first depositing a material on a tooling (such as a die or mold) of a predetermined shape up to a predetermined thickness, in which the tooling exhibits a plurality of protrusions that cause openings to be created in the first material, in which the first deposited material is formed at a first thickness which creates openings of a first interior dimension, and a second material is deposited on a tooling up to a second, greater thickness (if the tooling is of the same size and shape), or at least to a thickness that creates openings of a second interior dimension that is smaller than the first interior dimension, after which the first and second materials are released from their toolings then stacked together such that their respective openings are aligned, after which a moldable (third) material is placed against a surface formed by both of the first material and second material layers, and finally directing a high pressure gas or liquid through the openings of the second material, thereby forming holes in the moldable material of a size controlled by the second interior dimension, then solidifying and demolding the moldable material, which will exhibit an array of hollow microstructures.

It is still another advantage of the present invention to provide a methodology for forming a microstructure having an array of microelements with openings, in which the microstructure is formed by first depositing a material on a tooling (such as a die or mold) of a predetermined shape up to a predetermined thickness, in which the tooling exhibits a plurality of protrusions that cause openings to be created in the first material, in which the first material is deposited in a sufficient thickness to create rather small openings in the first material, then releasing the first material and placing a moldable (second) material against a surface formed by the first material and directing a high pressure gas or liquid through the rather small openings to form holes in the moldable material, then solidifying and demolding the moldable material, which will exhibit an array of hollow microstructures.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a method for constructing a microstructure is provided, in which the method comprises the following steps: (a) providing a moldable material to be formed into a predetermined shape; (b) during a molding procedure, forcing a predetermined fluid under pressure toward a surface of the moldable material, the predetermined fluid forming at least one opening at the surface; and (c) substantially solidifying the moldable material while the pressurized predetermined fluid continues to flow toward the surface, thereby forming a solid microstructure which includes the at least one opening at the surface.

In accordance with another aspect of the present invention, a method for constructing a microstructure is provided, in which the method comprises the following steps: (a) providing a tooling structure having a first surface and a second surface opposite the first surface, and having a substrate having a plurality of protrusions formed upon the first surface, the plurality of protrusions exhibiting at least one height; (b) depositing a material upon the first surface of the tooling structure, the material having a thickness that is generally less than the at least one height of the plurality of protrusions; and (c) separating the material from the tooling structure to form a micromold, the micromold exhibiting a first plurality of openings that correspond to a portion of a three-dimensional negative form of the plurality of protrusions of the tooling structure along the thickness of the material.

In accordance with yet another aspect of the present invention, a method for constructing a microstructure is provided, in which the method comprises the following steps: (a) providing a tooling structure having a first surface and a second surface opposite the first surface, and having a first substrate having a plurality of protrusions formed upon the first surface, the plurality of protrusions exhibiting at least one height; (b) depositing a first material upon the first surface of the tooling structure, the first material having a thickness that is generally less than the at least one height of the plurality of protrusions; (c) releasing the first material from the tooling structure, the first material exhibiting a plurality of openings that correspond to a portion of a three-dimensional negative form of the plurality of protrusions of the tooling structure along the thickness of the first material, the plurality of openings exhibiting at least one predetermined inner area proximal to a third surface of the first material; (d) providing a backing member at a predetermined and spaced-apart distance from a fourth surface of the first material, the fourth surface being opposite the third surface of the first material, the backing member exhibiting comparatively little porosity with respect to a moldable second material, but exhibiting substantial porosity with respect to a predetermined fluid; (e) introducing the moldable second material between the backing member and the fourth surface of the first material, and forcing the predetermined fluid under pressure through the plurality of openings of the first material to form at least one channel in the second material between the first material and the backing member, and substantially solidifying the second material while the pressurized predetermined fluid continues to flow through the plurality of openings; and (f) separating the solidified second material from the backing member and the first material, the solidified second material exhibiting a second substrate and exhibiting a plurality of microelements that substantially correspond in size and shape to a three-dimensional negative form of the plurality of openings in the first material, and further exhibiting the at least one channel running completely through the second substrate and at least one of the plurality of microelements.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE PREFERRED EMBODIMENT

Reference will now be made in detail to the present preferred embodiment of the invention, an example of which is illustrated in the accompanying drawings, wherein like numerals indicate the same elements throughout the views.

As described below, the present invention includes several different methodologies for manufacturing hollow microneedles (or "microelements"), in which such microneedles can be of various lengths. The microneedles can be, for example, as long as 2000 microns or 3000 microns, or as short as, for example, one-tenth of a micron. (A micron is a micrometer, which is $10^{-6}$ meters.) The lengths of the microelements can be substantially constant over the entire array if desired, or the lengths can vary over the array for a particular application. The maximum desired length will typically depend upon the particular application to which the microstructure will be used, and for example, it may be desirable to limit the length so that the microelements will not completely penetrate the stratum corneum layer of animal (e.g., human) skin.

It should be noted that some applications for microstructures does not involve penetrating the skin at all. For example, an exfoliation application would tend to remove substances from the outer skin, perhaps including hair. At the same time, a fluidic compound could be applied to the skin.

The shapes of the microneedles can be made using various materials, even including metal if desired. The final array structure that contains multiple microneedles/microelements is generally referred to herein as a "microstructure."

Figure 1:
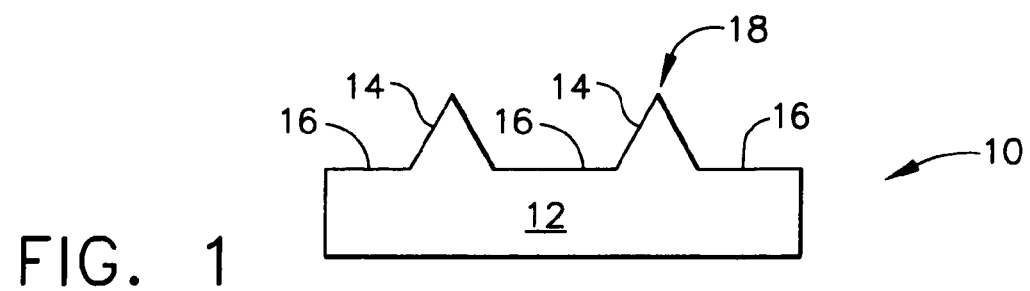
FIGS. 1-6 illustrate various steps in a process for creating an array of microelements on a microstructure, in which a material is deposited on a pre-shaped tooling, and then released from that tooling and covered with a mask having a plurality of openings, after which a layer of moldable material is placed against the surface of the combination, and pressurized gas or liquid is directed to create openings through the moldable material at locations where the formed microelements project from a substrate. All of these views are elevational cross-section views.

Referring now to FIG. 1, a pre-shaped tooling is prepared in a manner that one might prepare a mold or die for a plastic molding or a metal die-casting procedure. The tooling is generally designated by the reference numeral 10, and exhibits a substrate 12 which has a pair of pyramidal shaped protrusions 14 that end in an uppermost peak 18. (It will be understood that this tooling 10 will actually contain hundreds, if not thousands, of such protrusions 14.) The upper planar surface between the protrusions 14 are indicated at the reference numeral 16. The tooling 10 could be machined or etched in such a manner so that the final shape of the projections (protrusions) 14 will represent a desired shape or shapes of microstructures to be formed, in which these shapes could be of any manner desired by a system designer, such as pyramids, cones, cylinders, and/or wedges. Of course, combinations of shapes could be made or formed as protrusions on the same substrate 12. The material of the tooling could be metallic, ceramic, or silicon, or perhaps some other type of material, as desired by the system designer.

Figure 2:
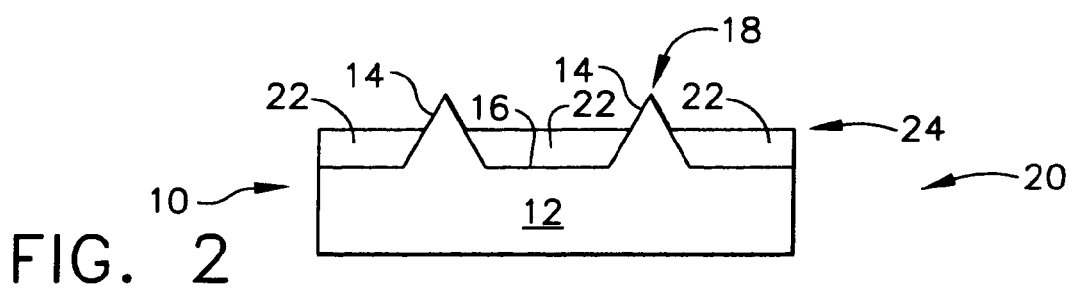

Referring now to FIG. 2, a second material 22 is deposited on the tooling 10 using a process such as electroplating, spin coating, or vapor deposition. The overall resulting structure is generally designated by the reference numeral 20, and the second material 22 is formed so as to exhibit a predetermined thickness above the planar surfaces 16, in which the predetermined thickness is illustrated at the reference arrow 24.

The second material 22 forms a partial negative micromold from the original tooling 10, and its height will be controlled to a predetermined value by any number of methodologies that are known in the art. This step could even be accomplished by using a plastic injection molding procedure, which would require a second mold half to mate against the upper surface of the material 22 and the upper surfaces of the projections 14. However, such a molding (or even casting) procedure is not specifically required for the present invention, although easily accomplished within the principles of the present invention.

Figure 3:
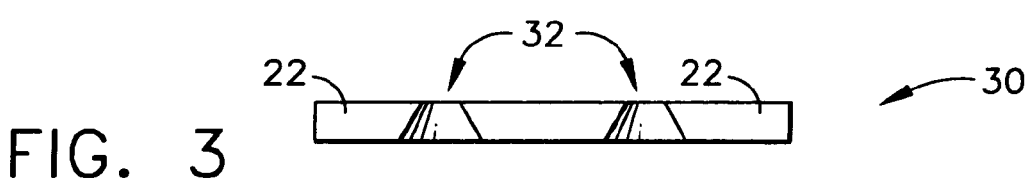

Referring now to FIG. 3, the deposited second material 22 has been separated or detached from the tooling, and now is generally designated by the reference numeral 30. Once detached, this layer of second material 22 will be substantially planar on both its top and bottom surfaces, and will also exhibit openings therethrough, as indicated at the reference arrows 32. These openings 32 will have a shape that is determined by the shape of the protrusions 14 of the original tooling 10, i.e., a three-dimensional negative shape or "form."

Figure 4:
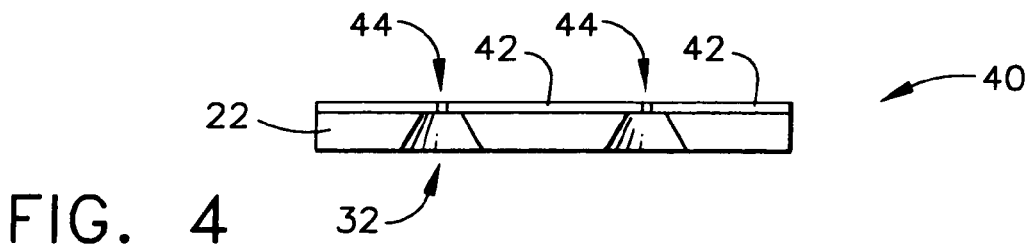

Referring now to FIG. 4, a mask layer is placed on the upper surface of the material 22, in which this mask is substantially planar and exhibits openings. The overall combination is generally designated by the reference numeral 40. The mask itself is designated by the reference numeral 42, and its openings by the reference arrows 44. At least some of the openings 44 are to be substantially aligned with some of the openings 32 of the material 22, such that the circumference (if circular) of the openings 44 will align within the area or perimeter of the circumference (if circular) of the openings 32. Since these structures are to be relatively small in overall size (and therefore referred to as "microstructures"), the inner perimeters or areas of openings 32 and 44 should be substantially "well-aligned."

Figure 5:
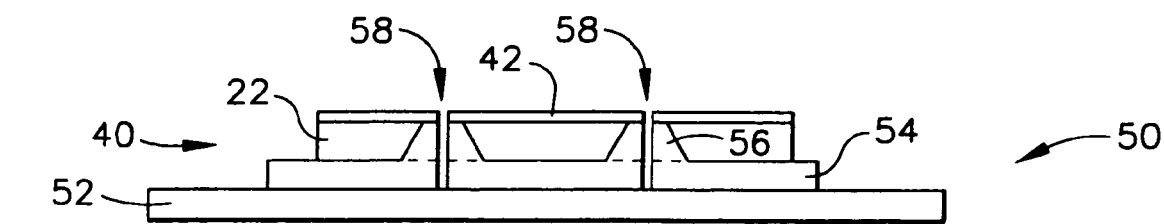

Referring now to FIG. 5, the structure 40 is now used in a molding procedure in which a bottom mold-half (or "backing plate") 52 is provided, and moldable material is placed between this backing half and the upper structure 40. This overall combination is generally designated by the reference numeral 50. After the structure 40 is positioned in a predetermined spaced-apart location with respect to the backing plate 52, a moldable material 54 is interjected or introduced therebetween, which fills up the substantially planar area between the material (micromold) 22 and the backing plate 52, as well as filling the volumetric spaces 56. Before the moldable material 54 hardens, a pressurized fluid (e.g., a high pressure gas or liquid) is directed through the openings 44 at locations generally designated by the reference numeral 58 on FIG. 5.

This high pressure gas or liquid will pass through the openings 44 and down through the backing plate 52, which could be manufactured of a substantially porous media with respect to the high pressure gas or liquid. Of course, in this arrangement the backing plate 52 cannot be substantially porous with respect to the moldable material 54 itself. That is, backing plate 52 should exhibit comparatively little porosity characteristics with regard to the flowability of moldable material 54 having a capability to leak therethrough perhaps some leakage would be permissible, but it would likely complicate the manufacturing process.

In some processes, it may be best if the backing plate 52 allows the pressurized gas or liquid to flow therethrough without causing a significant backpressure, which otherwise would of course add to the power requirements for the process of manufacturing, as well as needing a larger capacity pump, or fan ("blower") and motor combination. However, this is not a strict requirement—a substantially solid (non-porous) backing plate (with respect to the pressurized gas/liquid) might have other advantages, and still nevertheless be used in the present invention along with the appropriate pressure source for the fluid to be directed through the openings 44. If there is no need to maintain a fairly precise constant inner diameter of the through-holes 58 that will be formed in the moldable material 54, then certainly a non-porous backing plate 52 could be used in an alternative arrangement. In this alternative arrangement, the bottom-most portions (in the views) of the through-holes 58 may exhibit a smaller open (inner) area than at the top-most (in the views) portions of the same through-holes; however, if the bottom-most openings are sufficiently large to allow a predetermined molecule size (of a fluid) to pass therethrough, then such an arrangement will be sufficient.

As the moldable material 54 fills all of the space between material (micromold) 22 and backing plate 52, including the shaped volumes at 56, and while the high pressure gas or liquid is blown through the openings at 58 thus forming channels therethrough, the entire structure 50 is somewhat cooled so that the moldable material will harden. Once the moldable material 54 solidifies, it will be released from the "mold halves" 22 and 52, thereby exhibiting a shape illustrated in FIG. 6, generally designated by the reference numeral 60. The moldable material now exhibits a substrate 54 and multiple microelements 56 that project or protrude from the substrate 54. Each of the microelements 56 exhibits a hollow through-hole 58. These microelements 56 are designed so as to penetrate the outer layers of animal skin (e.g., through the stratum corneum of human skin), and the openings or through-holes 58 will allow for a fluid to be dispensed through the skin barrier or membrane barrier of the tissue that has been penetrated by the microelements 56. As noted above, the microelements 56 can be made to any desired shape, including hollow cylinders, or individual pyramidal shapes with through-holes. The actual material used to form the microstructure 60 would typically be a moldable plastic or polymer, although other materials could be utilized, even perhaps some type of metal in a casting process (although the pressurized gas or liquid that would form the through-holes in metal would indeed require a very high pressure to be applied, or for a chemical reaction to additionally be created during the forming and cooling stages of the process).

As noted above, the fluid itself can consist of a gas or liquid, such as a high pressure liquid or a hot gas that forms streams (e.g., fluid streams) through the openings 44, and which are used to mechanically force openings 58 through the moldable material while it is still in a mainly fluidic state (i.e., before solidifying). The pressurized fluid could comprise a heated gas, such as steam, or perhaps a heated liquid or a liquid solvent. As an alternative, a gas or liquid (fluidic) stream that tends to chemically dissolve the moldable material 54 could be used, including a situation where the "moldable" material 54 turns out to consist of a metal.

When viewing FIG. 4, it can be seen that the mask plate 42 has portions that in essence "overhang" the tops of the openings 32 of the bottom layer (i.e., micromold) 22, in the structure 40. This "overhang" allows a reusable mask plate 42 to provide smaller openings 44 that will define the wall thickness and inner perimeter (and inner area) of the hollow microstructures that are formed by the time the process reaches FIG. 6. In other words, the inner dimensions of the channels 58 are substantially dependent on the interior perimeter (e.g., the inner diameter, if circular) of the openings 44 in the mask plate 42, and not on the interior perimeter (e.g., the inner diameter, if circular) of the openings 32 in the structure 30 of FIG. 3.

It will be understood that the shapes and angles depicted for the openings 32 and 44 are for purposes of illustration and explanation, and that various other shapes and angles could be used without departing from the principles of the present invention. Moreover, the ratio of the inner dimensions of these openings 32 and 44 are also for purposes of illustration and explanation, and that various other ratios could be used without departing from the principles of the present invention. Certainly, virtually any microstructure dimensions could be used for the tooling protrusion 14 sizes, the thickness 24 of the material 22, and the thickness of the substrate 54 and length of the microelements 56 of the final microstructure 60, and are thus within the contemplation of the inventors.

A second embodiment that illustrates a procedure for forming microstructures with multiple microelements is illustrated in FIGS. 7-12, and will now be discussed in detail.

Figure 7:
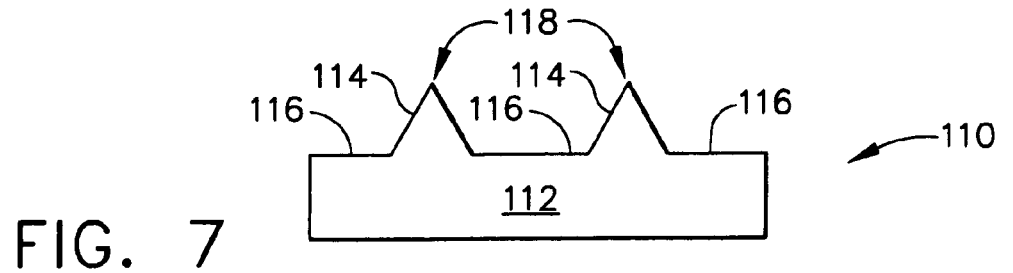
FIGS. 7-12 illustrate various steps in a process for creating an array of microelements on a microstructure, in which a material is deposited on a pre-shaped tooling, and then released from that tooling and covered with a mask having a plurality of openings, in which the mask exhibits a short hollow protrusion near the opening therein, after which a layer of moldable material is placed against the surface of the combination, and pressurized gas or liquid is directed to create openings through the moldable material at locations where the formed microelements project from a substrate. All of these views are elevational cross-section views.

Referring now to FIG. 7, a pre-shaped tooling is prepared in a manner that one might prepare a mold or die for a plastic molding or a metal die-casting procedure. The tooling is generally designated by the reference numeral 110, and exhibits a substrate 112 which has a pair of pyramidal shaped protrusions 114 that end in an uppermost peak 118. (It will be understood that this tooling 110 will actually contain hundreds, if not thousands, of such protrusions 114.) The upper planar surface between the protrusions 114 are indicated at the reference numeral 116. The tooling 110 could be machined or etched in such a manner so that the final shape of the projections (protrusions) 114 will represent a desired shape or shapes of microstructures to be formed, in which these shapes could be of any manner desired by a system designer, such as pyramids, cones, cylinders, and/or wedges. Of course, combinations of shapes could be made or formed as protrusions on the same substrate 112. The material of the tooling could be metallic, ceramic, or silicon, or perhaps some other type of material, as desired by the system designer.

Figure 8:
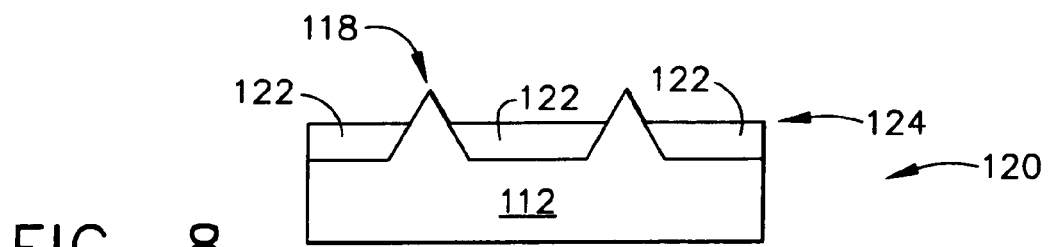

Referring now to FIG. 8 a second material 122 is deposited on the tooling 110 using a process such as electroplating, spin coating, or vapor deposition. The overall resulting structure is generally designated by the reference numeral 120, and the second material 122 is formed so as to exhibit a predetermined thickness above the planar surfaces 116, in which the predetermined thickness is illustrated at the reference arrow 124.

The second material 122 forms a partial negative micromold from the original tooling 110, and its height will be controlled to a predetermined value by any number of methodologies that are known in the art. This step could even be accomplished by using a plastic injection molding procedure, which would require a second mold half to mate against the upper surface of the material (micromold) 122 and the upper surfaces of the projections 114. However, such a molding (or even casting) procedure is not specifically required for the present invention, although easily accomplished within the principles of the present invention.

Figure 9:
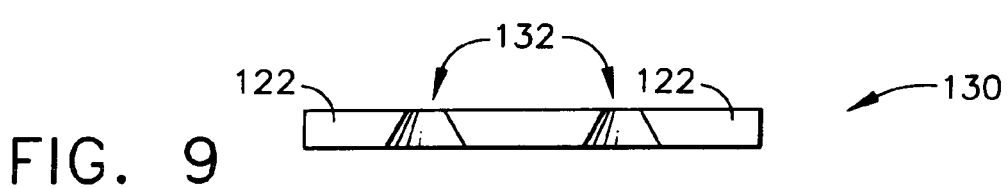

Referring now to FIG. 9, the deposited second material 122 has been separated or detached from the tooling, and now is generally designated by the reference numeral 130. Once detached, this layer of second material 122 will be substantially planar on both its top and bottom surfaces, and will also exhibit openings therethrough, as indicated at the reference arrows 132. These openings 132 will have a shape that is determined by the shape of the protrusions 114 of the original tooling 110, i.e., a three-dimensional negative shape or "form."

Figure 10:
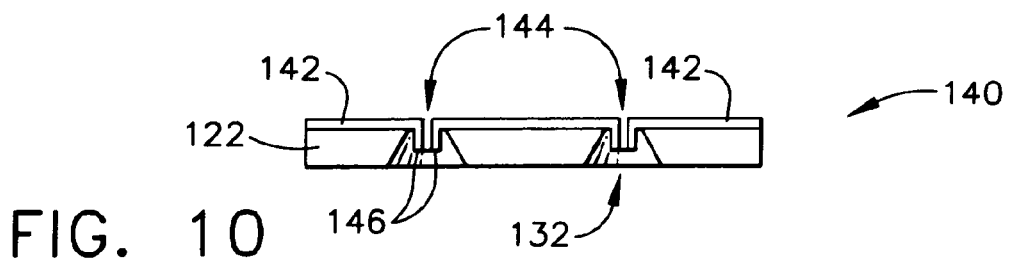

Referring now to FIG. 10, a mask layer is placed on the upper surface of the material 122, in which this mask is substantially planar and exhibits openings. The overall combination is generally designated by the reference numeral 140. The mask itself is designated by the reference numeral 142, and its openings by the reference arrows 144. At least some of the openings 144 are to be substantially aligned with some of the openings 132 of the material 122, such that the circumference (if circular) or area of the openings 144 will align within the perimeter of the circumference (if circular) or area of the openings 132. Since these structures are to be relatively small in overall size (and therefore referred to as "microstructures"), the inner perimeters/areas of openings 132 and 144 should be substantially "well-aligned."

The mask plate 142 has a somewhat different shape than the earlier mask plate 42, which was discussed above in reference to FIG. 4. In FIG. 10, it can be seen that the mask plate 142 not only exhibits openings at 144, but also exhibits a perpendicular structure that protrudes in a downward direction (as seen in FIG. 10), forming a hollow protrusion into the volume occupied by the opening 132 in the layer of material 122. This protrusion 146 will ultimately create the shape of the microelements that will be formed from this structure 140, and that shape will be somewhat different than illustrated in FIG. 6.

Figure 11:
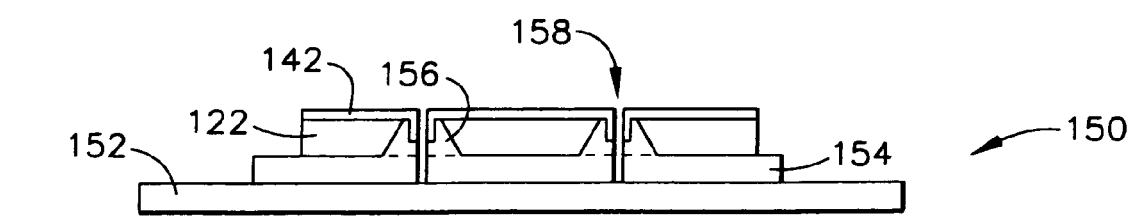

Referring now to FIG. 11, the structure 140 is now used in a molding procedure in which a bottom mold-half (or "backing plate") 152 is provided, and moldable material is placed between this backing half and the upper structure 140. This overall combination is generally designated by the reference numeral 150. After the structure 140 is positioned in a predetermined spaced-apart location with respect to the backing plate 152, a moldable material 154 is interjected or introduced therebetween, which fills up the substantially planar area between the material 122 and the backing plate 152, as well as filling the volumetric spaces 156. Before the moldable material 154 hardens, a pressurized fluid (e.g., a high pressure gas or liquid) is directed through the openings 144 at locations generally designated by the reference numeral 158 on FIG. 11. This high pressure gas or liquid will pass through the openings 144 and down through the backing plate 152, which could be manufactured of a substantially porous media with respect to the high pressure gas or liquid. Of course, the backing plate 152 cannot be substantially porous with respect to the moldable material 154 itself. Alternatively, the backing plate 152 could have a non-porous characteristic with respect to the pressurized gas/liquid, along with an appropriate pressure source.

As the moldable material 154 fills all of the space between material 122 and backing plate 152, including the shaped volumes at 156, and while the high pressure gas or liquid is blown through the openings at 158 thus forming channels therethrough, the entire structure 150 is somewhat cooled so that the moldable material will harden. Once the moldable material 154 solidifies, it will be released from the "mold halves" 122 and 152, thereby exhibiting a shape illustrated in FIG. 12, generally designated by the reference numeral 160. The moldable material now exhibits a substrate 154 and multiple microelements 156 that project or protrude from the substrate 154. Each of the microelements 156 exhibits a hollow through-hole 158. These microelements 156 are designed so as to penetrate the outer layers of animal skin (e.g., through the stratum corneum of human skin), and the openings or through-holes 158 will allow for a fluid to be dispensed through the skin barrier or membrane barrier of the tissue that has been penetrated by the microelements 156.

As noted above, the microelements 156 can be made to any desired shape, including hollow cylinders, or individual pyramidal shapes with through-holes. The actual material used to form the microstructure 160 would typically be a moldable plastic or polymer, although other materials could be utilized, even perhaps some type of metal in a casting process (although the pressurized gas or liquid that would form the through-holes in metal would indeed require a very high pressure to be applied, or a chemical reaction to additionally be created, during the forming and cooling stages of the process).

Figure 6:
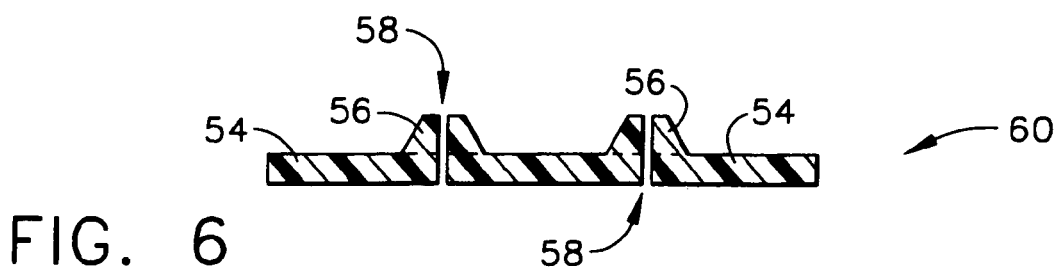
Figure 12:
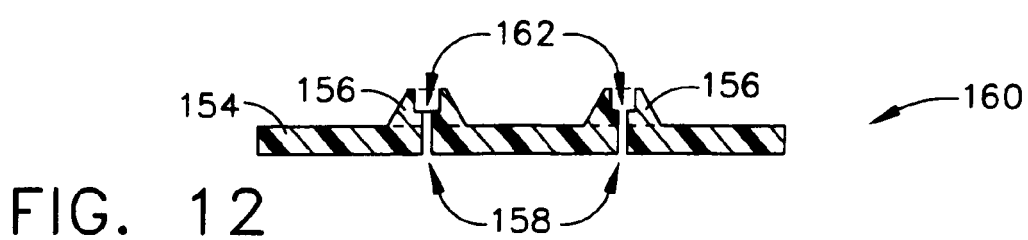

The shape of the openings of the individual microelements 156 is somewhat different than depicted at 56 in FIG. 6, in that the opening at 162 is larger in its inner dimension, as illustrated at 162 on FIG. 12. In other words, the interior perimeter or area of the portion of the through-hole at 158 is smaller than the interior perimeter or area of the portion of the through-hole at 162, which also provides for sharper edges at the uppermost tips of the microelements 156.

When viewing FIG. 10, it can be seen that the mask plate 142 has portions that in essence "overhang" the tops of the openings 132 of the bottom layer 122, in the structure 140. This "overhang" allows a reusable mask plate 142 to provide smaller openings 144 and protrusions 146 that will define the wall thicknesses and inner perimeters (and inner areas) of the hollow microstructures that are formed by the time the process reaches FIG. 12. In other words, the inner dimensions of the channels 158 and 162 are substantially dependent on the interior perimeters (e.g., the inner diameters, if circular) of the openings 144 and protrusions 146 in the mask plate 142, and not on the interior perimeters (e.g., the inner diameters, if circular) of the openings 132 in the structure 130 of FIG. 9.

It will be understood that the shapes and angles depicted for the openings 132 and 144 are for purposes of illustration and explanation, and that various other shapes and angles could be used without departing from the principles of the present invention. Moreover, the ratio of the inner dimensions of these openings 132 and 144 are also for purposes of illustration and explanation, and that various other ratios could be used without departing from the principles of the present invention. Certainly, virtually any microstructure dimensions could be used for the tooling protrusion 114 sizes, the thickness 124 of the material 122, the protrusions 146 of the mask, and the thickness of the substrate 154 and length of the microelements 156 of the final microstructure 160, and are thus within the contemplation of the inventors.

Figure 13:
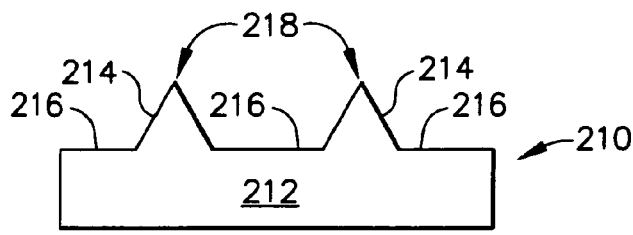
FIGS. 13-20 illustrate various steps in a process for creating an array of microelements on a microstructure, in which a first material is deposited on a pre-shaped tooling up to a first predetermined depth, and a second material is deposited on a pre-shaped tooling up to a second different depth, and after the two materials are released from their respective toolings, they are abutted against one another such that their openings are well aligned. After that has occurred, a moldable (third) material is placed against the surface of the first material, while high pressure gas or liquid is directed through openings in the second material, thereby forming through-holes in the moldable material, and when this moldable material is solidified and released, it exhibits hollow microelements that protrude from a substrate. All of these views are elevational cross-section views.

A third embodiment that illustrates a procedure for forming microstructures with multiple microelements is illustrated in FIGS. 13-20, and will now be discussed in detail. Referring now to FIG. 13, a tooling structure generally designated by the reference numeral 210 is provided having a predetermined shape for its upper surface, in which its substrate 212 has a relatively planar upper surface at 216 along with projections 214 that have uppermost peaks at 218.

Figure 14:
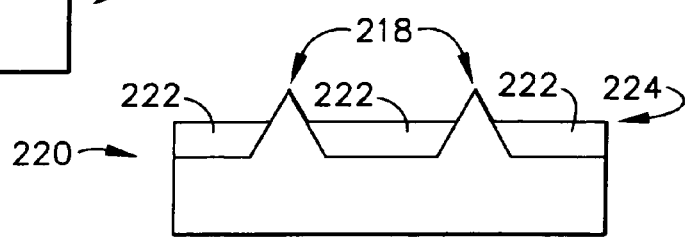

Referring now to FIG. 14, a second material 222 is deposited on the tooling 210 using a process such as electroplating, spin coating, or vapor deposition. The overall resulting structure is generally designated by the reference numeral 220, and the second material 222 is formed so as to exhibit a predetermined thickness above the planar surfaces 216, in which the predetermined thickness is illustrated at the reference arrow 224.

The second material 222 forms a partial negative mold from the original tooling 210, and its height will be controlled to a predetermined value by any number of methodologies that are known in the art. This step could even be accomplished by using a plastic injection molding procedure, which would require a second mold half to mate against the upper surface of the material 222 and the upper surfaces of the projections 214. However, such a molding (or even casting) procedure is not specifically required for the present invention, although easily accomplished within the principles of the present invention.

Figure 15:
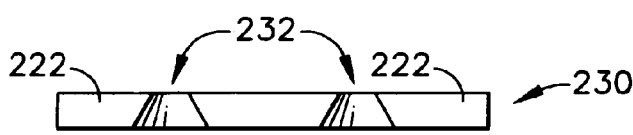

Referring now to FIG. 15, the deposited second material 222 has been separated or detached from the tooling, and now is generally designated by the reference numeral 230. Once detached, this layer of second material 222 will be substantially planar on both its top and bottom surfaces, and will also exhibit openings therethrough, as indicated at the reference arrows 232. These openings 232 will have a shape that is determined by the shape of the protrusions 214 of the original tooling 210, i.e., a three-dimensional negative shape or "form."

Figure 16:
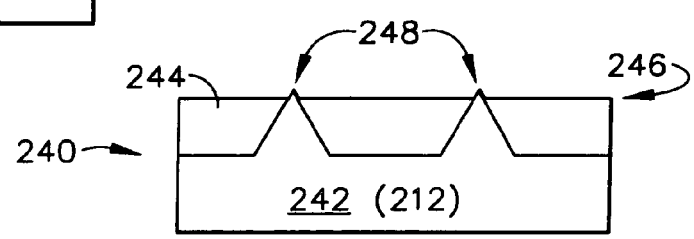
Figure 17:
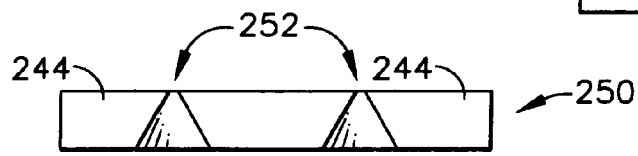

The same type of tooling 212 (i.e., in size and shape) can also be used again in which a layer of material 244 is deposited to a greater thickness, as illustrated in FIG. 16, in which this structure is generally designated by the reference numeral 240. The tooling has a bottom structure 242 having multiple protrusions, with peaks at 248. The deposited material 244 is allowed to acquire a thickness so that its uppermost dimension is illustrated at 246, and approaches the height of the peaks 248. When this deposited layer of material 244 is detached from the tooling 242, it will exhibit fairly small openings at 252, as illustrated in FIG. 17. This deposited material 244 is generally designated by the reference numeral 250 on FIG. 17, and will both be thicker than the material 222 of FIG. 15, and will exhibit smaller openings at 252 as compared to the openings 232 of FIG. 15.

As an obvious alternative, the tooling 242 could exhibit a somewhat different size and/or shape from that of tooling 212, such that the height 246 of the deposited material 244 (above the planar surface 247) could be precisely the same as the height 224 (above the planar surface 216) of the deposited material 222. In that circumstance, it would still be desirable for the openings 252 to be the controlling dimension for the later process steps discussed below in reference to FIGS. 18-20 (i.e., openings 252 should be smaller in their interior perimeters or inner areas than openings 232). This could be simply accomplished by providing a different shape and/or size to the projections 249, having their peaks at 248.

Figure 18:
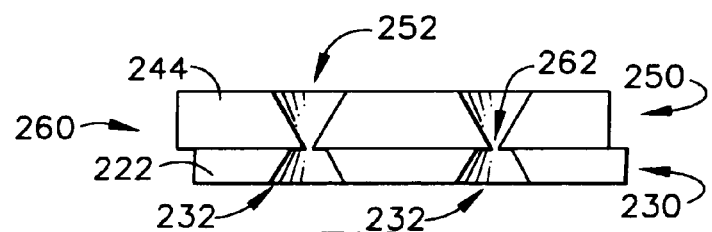

These structures 230 and 250 are now abutted against one another as illustrated in FIG. 18, thereby producing a structure generally designated by the reference numeral 260. The bottom structure 230 includes the larger openings 232, while the upper structure 250 exhibits the thicker layer of material 244 with the openings 252 that narrow or taper down to a smaller interior perimeter/area, as seen at the reference arrow 262. The perimeter/area of openings at 262 should generally be aligned within the perimeter/area of openings 232, and thus these structures 230 and 250 should be substantially well-aligned. These two layers 230 and 250 are not necessarily to be permanently attached or affixed to one another, however, they are to be held firmly in place during the next step of the procedure, which is illustrated in FIG. 19.

Figure 19:
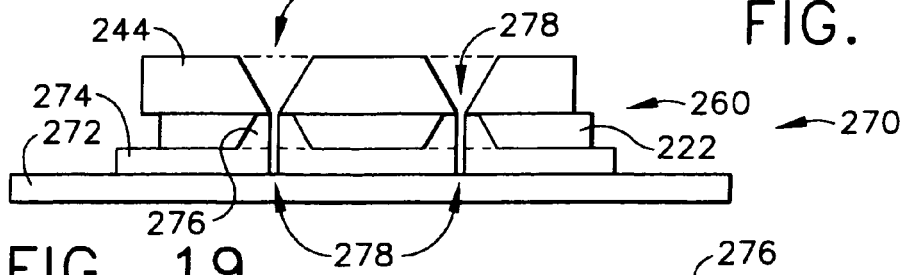

In FIG. 19, a bottom mold-half or backing plate 272 is brought to a predetermined spaced-apart position from the structure 260, and a moldable material 274 is interjected or introduced therebetween. This overall structure is illustrated in FIG. 19, and generally designated by the reference numeral 270. While the backing plate 272 is in position, the moldable material 274 is introduced (perhaps by an injection molding process) such that it fills the volume between the layer 222 and the backing plate 272, as well as the volume at 276 that was formed by the opening 232 in the layer 230. While this introduction of moldable material is proceeding, a high pressure fluid (i.e., a gas or liquid) is directed through the openings 252 and down through the openings 232 (which is seen as subsisting of moldable material 276), thereby forming channels 278 in the moldable material. This high pressure gas or liquid thereby forms the hollow channels 278, while passing through the backing plate 272, which could be composed of a porous media with respect to the gas or liquid streams. Of course, the backing plate 272 is not substantially porous with respect to the moldable material 274. As noted above, a backing plate such as plate 272 need not necessarily be porous with respect to the pressurized gas/liquid, when used with an appropriate pressure source for the pressurized fluid.

Figure 20:
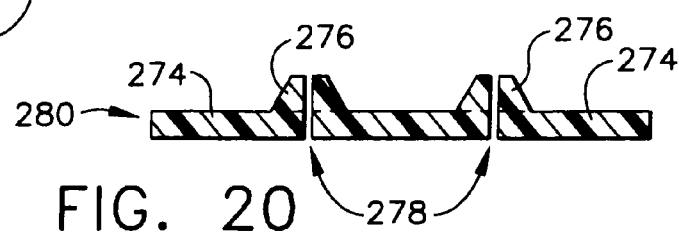

The high-pressure fluid continues to flow while the moldable material is cooled until it solidifies, such that the channels 278 will become permanent. After the moldable material 274 has solidified, it will be released from the mold halves formed by the elements 260 and 272, thereby providing the "final" structure generally designated by the reference numeral 280, illustrated in FIG. 20. As can be seen in FIG. 20, the microstructure 280 includes a substrate 274 and multiple microelements 276, which have through-holes or openings at 278. In a similar manner to the procedures and structures discussed above with respect to FIGS. 1-12, the microelements 276 can be of virtually any size and shape chosen by a system designer, including conical, pyramidal, cylindrical, or even wedged shapes. Moreover, a combination of such shapes can be used upon a single substrate 274 to form a single microstructure 280 with microelements of multiple shapes, or in multiple patterns of arrays.

It will be understood that the smaller openings 252 of the layer 244 essentially act as a "mask," such that they "overhang" the larger openings 232 in the layer 222, as seen in FIG. 18. These smaller openings at the narrowest portions of the openings 252 are indicated at the reference arrows 262, and it is the interior perimeter at these narrow-most (or tapered) openings 262 that will define the wall thickness and inner dimensions (e.g., open areas) of the microelements 276 and the through-holes 278.

It will be understood that the shapes and angles depicted for the openings 232 and 252 are for purposes of illustration and explanation, and that various other shapes and angles could be used without departing from the principles of the present invention. Moreover, the ratio of the inner dimensions of these openings 232 and 252 are also for purposes of illustration and explanation, and that various other ratios could be used without departing from the principles of the present invention. Certainly, virtually any microstructure dimensions could be used for the tooling protrusion 214 sizes, the thicknesses 224 and 246 of the materials 222 and 246, and the thickness of the substrate 274 and length of the microelements 276 of the final microstructure 280, and are thus within the contemplation of the inventors.

Figure 21:
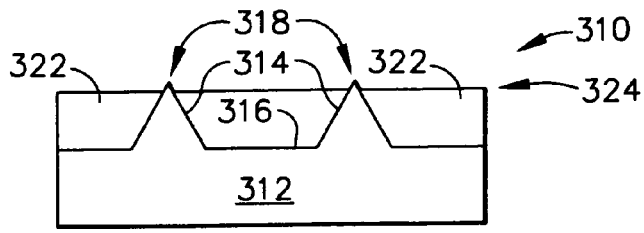
FIGS. 21-24 illustrate various steps in a process for creating an array of microelements on a microstructure, in which a first material is deposited on a pre-shaped tooling up to a predetermined thickness, and once the material is released, it will become a mold shape having a plurality of small openings. A moldable (second) material is then placed against this released, deposited material, and pressurized gas or liquid is directed through the openings in the first material, thereby forming through-holes in the moldable material. When the moldable material is solidified and released, it exhibits a plurality of hollow microelements that protrude from a substrate. All of these views are elevational cross-section views.
Figure 22:
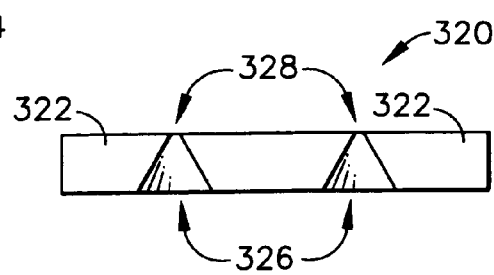

A fourth embodiment that illustrates a procedure for forming microstructures with multiple microelements is illustrated in FIGS. 21-24, and will now be discussed in detail. Referring now to FIG. 21, a tooling 312 is provided with planar surfaces 316 and multiple protrusions or projections 314 having peaks at 318. A second material 322 is deposited on this tooling, thereby producing the structure generally designated by the reference numeral 310 in FIG. 21. As it is being deposited, the second material 322 is allowed to come up to a predetermined thickness, such that its height at the reference arrow 324 is almost the same as the height of the peaks 318 of the tooling 312. When the deposited material 322 is separated from the tooling 312, it produces a structure generally designated by the reference numeral 320, as illustrated in FIG. 22. The openings 326 that have been formed in the material 322 taper down to their narrowest points at the reference arrows 328. These tapered openings 328 can be controlled merely by controlling the amount of material, or the height of the material, that defines the dimension 324 in FIG. 21. If desired, the process to form the structure 310 in FIG. 21 could involve a plastic injection molding procedure, rather than some type of depositing procedure. In addition, a die-casting methodology could be used, if it is desired for the material used for the structure 320 to comprise metal, rather than a moldable plastic or polymer material. If either injection molding or die-casting is to be used, then a top "mold-half" or "die-half" will also be needed.

Figure 23:
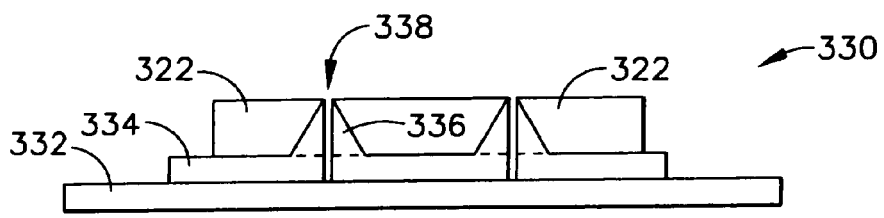
Figure 24:
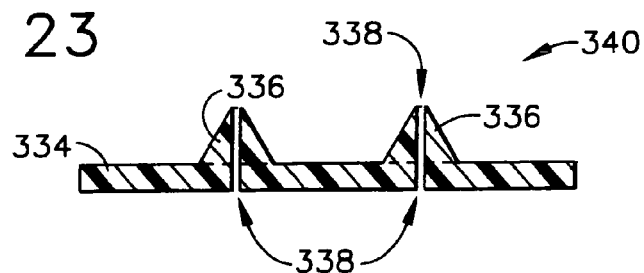

Referring now to FIG. 23, the structural layer 322 is brought within a predetermined spaced-apart distance to a second mold-half or backing plate 332, and a moldable material is interjected therebetween, thus forming the structure generally designated by the reference numeral 330. The moldable material at 334 will fill the space between the top surface of the backing plate 332 and the bottom surfaces of the tooling 322, including the openings 326, which are filled by the moldable material at 336. While the moldable material is introduced, a high pressure gas or liquid is directed from above, and will pass through the relatively small openings 328 in the tooling 322, thereby forming channels 338 in the moldable material. This situation is maintained until the moldable material has completely filled the appropriate volume, and is then cooled so that it will solidify. Once the moldable material 334 has become a solid, the "mold halves" 322 and 332 will separate such that a structure 340 is released, as illustrated in FIG. 24. This microstructure 340 will include a substrate 334 that exhibits multiple microelements 336 which protrude or project above the upper planar surface, and in which these microelements 336 have through-openings at 338.

As can be seen from the above description, this embodiment of FIGS. 21-24 does not require a separate mask plate to help define the size and shape of the openings that are formed through the microelements 336. This not only eliminates a part or fixture while stepping through the inventive methodology in forming these microstructures, but also eliminates the requirement of aligning any type of mask plate with the earlier-formed tooling structure that is used to shape the microelements themselves. All that is required in this embodiment of FIGS. 21-24 is that the height of the initial material 322 (see FIG. 21) be properly controlled so that the size of the openings formed by the microelement projections 314 are of the correct non-circular perimeter (or correct diameter, if circular) or area when openings are formed at their narrowest extents, as at 328 (as seen in FIG. 22).

It will be understood that the shapes and angles depicted for the openings 328 are for purposes of illustration and explanation, and that various other shapes and angles could be used without departing from the principles of the present invention. Certainly, virtually any microstructure dimensions could be used for the tooling protrusion 314 sizes, the thickness 324 of the material 322, and the thickness of the substrate 334 and length of the microelements 336 of the final microstructure 340, and are thus within the contemplation of the inventors.

For all embodiments of the present invention, it will be understood that the high pressure gas or liquid that forms the through-holes in the moldable material can be of a continuous pressure, or can be of a pulsed pressure. Also, the high pressure fluid (gas or liquid) could instead be controlled for its time duration so as to create indentations, rather than through-holes (as discussed below in greater detail). In addition, the interjection of the moldable material can be accomplished by injection molding, or perhaps by embossing a film of moldable material, or even by casting, if desired. It will also be understood that the physical orientation of the mechanical elements in the illustrations of FIGS. 5, 11, 19, and 23 could be different from that illustrated, and in fact it could be oriented upside-down, or even at 90° or other angles, if desired.

Figure 25:
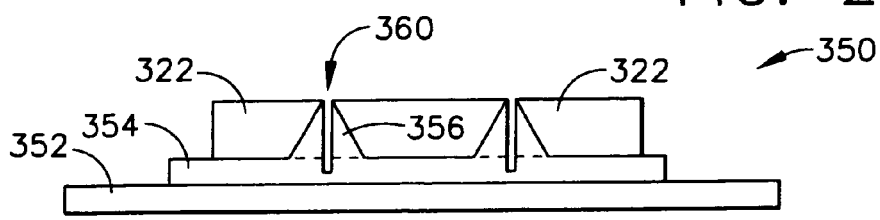
FIGS. 25-26 illustrate the final steps of an alternative process creating an array of microelements on a microstructure, in which the deposited material of FIG. 22 is used to create a microstructure having openings that do not extend entirely through the moldable material.
Figure 26:
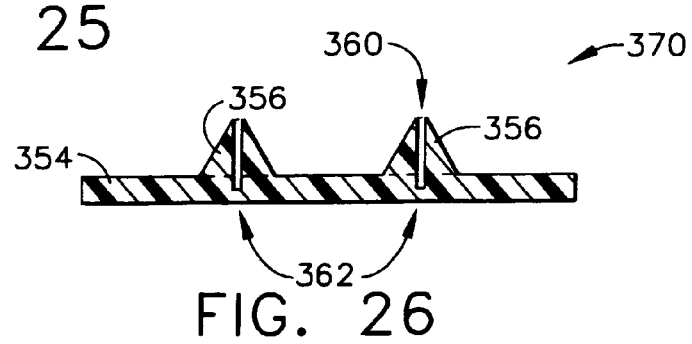

The tooling of FIG. 21 is used to create a microstructure shape 320 that is illustrated in FIG. 22, as discussed above. However, as noted above, it is not necessary to always create openings or holes that extend entirely through the final microstructure. An example of constructing such a structure is illustrated in FIGS. 25 and 26. In FIG. 25, the deposited material 322 is again used as a mold shape or mold-half, while a backing plate 352 provides the "bottom" mold shape (as seen in this view). Moldable material 354 is interposed between these mold shapes 322 and 352, thus creating the temporary structure generally designated by the reference numeral 350. In this particular process, it is not at all necessary or desired for the backing plate 352 to have any type of porous characteristics with respect to a pressurized fluid.

The moldable material at 354 will fill the space between the top surface of the backing plate 352 and the bottom surfaces of the tooling 322, including the openings 326, which are filled by the moldable material at 356. While the moldable material is introduced, a high pressure gas or liquid is directed from above, and will pass through the relatively small openings 328 in the tooling 322, thereby forming channels 360 in the moldable material. This situation is maintained until the moldable material has completely filled the appropriate volume, and is then cooled so that it will solidify. Once the moldable material 354 has become a solid, the "mold halves" 322 and 352 will separate such that a structure 370 is released, as illustrated in FIG. 26. This microstructure 340 will include a substrate 354 that exhibits multiple microelements 356 which protrude or project above the upper planar surface, and in which these microelements 356 have openings at 360.

In this alternative process, when the pressurized fluid is directed through the openings in the material 322, it is done in a manner such that the openings or channels 360 created in the shaped volume 356 will not extend completely through to the backing plate 352. A final microstructure 370 is provided, in which the openings or indentations 360 do not run completely through to the bottom surface of the substrate 354, and a portion (at 362) of solid material remains at the bottom-most extent of the openings 360. This can be accomplished by controlling the fluidic pressure and the time duration for sending the pressurized fluid through the openings 328, such that the moldable material is solidified before the openings/indentations 360 can form a complete channel through to the bottom of the substrate 354. The use of a pulsed pressure source could aid in constructing this microstructure. Such indentations (instead of through-holes) could be formed in conjunction with any of the embodiments disclosed herein.

It will be understood that the exact shapes of the projections of the tooling can vary from those illustrated in the figures, without departing from the principles of the present invention. Examples of possible shapes are disclosed in the patent documents noted above in the BACKGROUND, also assigned to The Procter & Gamble Company, which are incorporated by reference herein. It will also be understood that the relative ratios of openings for various hole or channel sizes can vary from those illustrated, without departing from the principles of the present invention. It will be further understood that the materials discussed above are merely examples, and virtually any type of moldable or castable material could be used in conjunction with the principles of the present invention to manufacture the microstructures using the methodologies described.

It will be further understood that the methodologies of the present invention extend to a process for making through-holes or indentations in a microstructure, whether or not these through-holes/indentations are physically located within a protrusion of that microstructure. In other words, such through-holes/indentations could be located along a portion of the microstructure's substrate that is otherwise substantially planar along its top and bottom surfaces. This is easily accomplished, for example, by creating some openings 44 in the mask plate 42 (see FIG. 4) that do not line up with openings 32 (see FIG. 3) in the tooling 30. In that situation, the pressurized fluid that is directed through the openings 44 would create some openings (not shown in FIG. 5) that extend through only the substrate 54 of the moldable material, and not through one of the protrusions 56. If it is not important that many or most of the protrusions 56 contain openings, then the "well-aligned" characteristic discussed above would not need to be maintained when constructing such microstructures.

In conclusion, the present invention offers a method for simultaneously creating openings and/or indentations in a moldable material, while that moldable material is actually having its shape formed and solidified. The present invention additionally offers a method for constructing a micromold by depositing material (e.g., by electroplating, spin coating, or vapor deposition onto a tooling structure having a predetermined shape, and then releasing the deposited material, which will thereby have acquired the physical shape that is a three-dimensional negative of the tooling structure's physical shape.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for constructing a microstructure comprising an array of microneedles designed to penetrate the stratum corneum of human skin, said method comprising: (a) providing a moldable material to be formed into a predetermined shape; (b) during a molding procedure, forcing a predetermined fluid under pressure toward a surface of said moldable material, said predetermined fluid forming at least one opening at said surface; and (c) substantially solidifying said moldable material while said pressurized predetermined fluid continues to flow toward said surface, thereby forming a solid microstructure which includes said at least one opening at said surface, wherein the solid microstructure has the predetermined shape comprising an array of microneedles protruding from a substrate wherein said microneedles are able to penetrate the stratum corneum of human skin.

2. The method as recited in claim 1, wherein: said at least one opening extends completely through said solid microstructure.

3. The method as recited in claim 1, wherein: said at least one opening forms an indentation that does not extend completely through said solid microstructure.

4. The method as recited in claim 1, wherein said molding procedure comprises one of: (a) injection molding, (b) embossing, and (c) die casting.

5. The method as recited in claim 1, further comprising: providing a micromold having a first mold-half and a second mold-half, said first mold-half including a plurality of openings through which said predetermined fluid is forced under pressure.

6. The method as recited in claim 5, wherein: said second mold-half comprises one of: (a) a material that is substantially non-porous with respect to said moldable material, but is substantially porous with respect to said predetermined fluid; and (b) a material that is substantially non-porous with respect to said moldable material, and is also substantially non-porous with respect to said predetermined fluid.

7. The method as recited in claim 5, wherein: (a) said moldable material is formed into a three-dimensional negative form of said first and second mold-halves, and comprises (i) a substrate having a first surface and a second surface opposite said first surface, and (ii) at least one protrusion extending from the first surface of said substrate; and (b) said at least one opening is physically located at one of: (i) one of said at least one protrusion, and (ii) along a substantially planar portion of the first surface of said substrate.

8. The method as recited in claim 7, wherein: said at least one protrusion exhibits a length in the range of 0.1-3000 microns.

9. A method for constructing a micromold, said method comprising: (a) providing a tooling structure having a first surface and a second surface opposite said first surface, and having a substrate having a plurality of protrusions formed upon said first surface, said plurality of protrusions exhibiting at least one height; (b) depositing a material upon the first surface of said tooling structure, said material having a thickness that is generally less than said at least one height of said plurality of protrusions; and (c) separating said material from said tooling structure to form a micromold, said micromold exhibiting a first plurality of openings that correspond to a portion of a three-dimensional negative form of said plurality of protrusions of the tooling structure along said thickness of said material, wherein said depositing step comprises one of: (a) electroplating; (b) spin coating; (c) vapor deposition; (d) injection molding; and (e) casting.

10. The method as recited in claim 9, further comprising: (d) providing a backing member; (e) introducing a moldable material between said micromold and said backing member; (f) during a molding procedure, forcing a predetermined fluid under pressure through said first plurality of openings in said micromold toward a surface of said moldable material, said predetermined fluid forming a second plurality of openings at said surface of said moldable material; and (g) substantially solidifying said moldable material while said pressurized predetermined fluid continues to flow toward said surface of said moldable material, thereby forming a solid microstructure which includes said second plurality of openings at said surface of said moldable material.

11. The method as recited in claim 10, wherein one of the following statements holds: (a) said second plurality of openings extend completely through said solid micro structure; (b) said second plurality of openings form at least one indentation that does not extend completely through said solid microstructure; or (c) a first group of the second plurality of openings extends completely through said solid microstructure, while a second group of the second plurality of openings forms at least one indentation that does not extend completely through said solid microstructure.

12. The method as recited in claim 10, wherein said molding procedure comprises one of: (a) injection molding, (b) embossing, and (c) die casting.

13. The method as recited in claim 10, further comprising: (h) providing a mask member which exhibits a third plurality of openings; (i) placing said mask member substantially against a surface of said micromold that faces away from said backing member, wherein by such placement, said third plurality of openings is substantially well-aligned with said first plurality of openings of said micromold; and (j) during said molding procedure, forcing said predetermined fluid under pressure through both said third plurality of openings of said mask member and said first plurality of openings of said micromold toward said third surface of said moldable material.

14. The method as recited in claim 13, wherein said mask member exhibits one of the following physical characteristics: (a) said mask member comprises a substantially flat plate; (b) said mask member exhibits a shape similar to said micromold, but inverted in orientation; and (c) at said surface between said mask member and micromold, an inner area of the third plurality of openings of said mask member is generally smaller than an inner area of the first plurality of openings of said micromold.

15. The method as recited in claim 10, wherein: said backing member comprises one of: (a) a material that is substantially non-porous with respect to said moldable material, but is substantially porous with respect to said predetermined fluid; and (b) a material that is substantially non-porous with respect to said moldable material, and is also substantially non-porous with respect to said predetermined fluid.

16. The method as recited in claim 10, wherein: (a) said moldable material is formed into a three-dimensional negative form of said backing member and said micromold, and comprises: (i) a substrate having said third surface and a fourth surface opposite said third surface, and (ii) a second plurality of protrusions extending from the third surface of said substrate; and (b) at least some of said second plurality of openings are physically located at one of: (i) one of said second plurality of protrusions, and (ii) along a substantially planar portion of the third surface of said substrate.

17. The method as recited in claim 16, wherein: said second plurality of protrusions exhibits a length in the range of 0.1-3000 microns.

18. A method for constructing a microstructure, said method comprising: (a) providing a tooling structure having a first surface and a second surface opposite said first surface, and having a first substrate having a plurality of protrusions formed upon said first surface, said plurality of protrusions exhibiting at least one height; (b) depositing a first material upon the first surface of said tooling structure, said first material having a thickness that is generally less than said at least one height of said plurality of protrusions; (c) releasing said first material from said tooling structure, said first material exhibiting a plurality of openings that correspond to a portion of a three-dimensional negative form of said plurality of protrusions of the tooling structure along said thickness of said first material, said plurality of openings exhibiting at least one predetermined inner area proximal to a first surface of said first material; (d) providing a backing member at a predetermined and spaced-apart distance from a second surface of said first material, said fourth surface being opposite said first surface of the first material, said backing member exhibiting comparatively little porosity with respect to a moldable second material, but exhibiting substantial porosity with respect to a predetermined fluid; (e) introducing said moldable second material between said backing member and the second surface of said first material, and forcing said predetermined fluid under pressure through said plurality of openings of the first material to form at least one channel in said second material between said first material and said backing member, and substantially solidifying said second material while said pressurized predetermined fluid continues to flow through said plurality of openings; and (f) separating said solidified second material from said backing member and said first material, said solidified second material exhibiting a second substrate and exhibiting a plurality of microelements that substantially correspond in size and shape to a three-dimensional negative form of said plurality of openings in the first material, and further exhibiting said at least one channel running completely through said second substrate and at least one of said plurality of micro elements.

19. The method as recited in claim 18, wherein said plurality of openings are smaller in area proximal to said first surface of said first material than they are in inner area proximal to said second surface of said first material.

* * * * *